United States Patent
Hagby

(10) Patent No.: US 10,765,454 B2
(45) Date of Patent: *Sep. 8, 2020

(54) SAMPLING NEEDLE

(71) Applicant: VITROLIFE SWEDEN AB, Gothenburg (SE)

(72) Inventor: Urban Hagby, Grabo (SE)

(73) Assignee: VITROLIFE SWEDEN AB, Gothenburg (SE)

( * ) Notice: Subject to any disclaimer, the term of this patent is extended or adjusted under 35 U.S.C. 154(b) by 238 days.

This patent is subject to a terminal disclaimer.

(21) Appl. No.: 15/884,776

(22) Filed: Jan. 31, 2018

(65) Prior Publication Data

US 2018/0146986 A1 May 31, 2018

Related U.S. Application Data

(63) Continuation of application No. 12/532,362, filed as application No. PCT/GB2008/000251 on Jan. 24, 2008, now Pat. No. 9,907,571.

(30) Foreign Application Priority Data

Sep. 28, 2007 (GB) .................................. 0719037.4

(51) Int. Cl.
  *A61B 17/435* (2006.01)
  *A61B 10/02* (2006.01)
  (Continued)

(52) U.S. Cl.
  CPC ........ *A61B 17/435* (2013.01); *A61B 10/0283* (2013.01); *A61B 17/425* (2013.01); *A61B 2010/045* (2013.01)

(58) Field of Classification Search
  CPC . A61B 17/425; A61B 17/435; A61B 10/0283; A61B 2010/045
  (Continued)

(56) References Cited

U.S. PATENT DOCUMENTS 3,540,447 A  11/1970 Howe
3,993,079 A  11/1976 de Gatztanondo
(Continued)

FOREIGN PATENT DOCUMENTS

EP  1323483 A2  7/2003
EP  1795127 A2  6/2007
(Continued)

OTHER PUBLICATIONS

Affidavit of Dr. Matts Wikland, submitted for related Japanese Application No. 2010-517473, affidavit dated Mar. 8, 2012;14 pages.
(Continued)

*Primary Examiner* — Navin Natnithithadha
*Assistant Examiner* — Sunita Reddy
(74) *Attorney, Agent, or Firm* — Pearne & Gordon LLP

(57) ABSTRACT

An oocyte retrieval needle is provided. The needle comprises a first tubular region in fluid communication with a second tubular region. The first tubular region comprises a sharp point leading end configured for insertion into a subject. The second tubular region comprises an open trailing end. The leading and trailing ends form respective opposite ends of the needle. Internal passages of the first and second tubular regions form a continuous open passage extending from the leading end to the trailing end. The first tubular region has an outer diameter which is less than an outer diameter of the second tubular region and the internal passage of the first tubular region has an inner, luminal diameter which is less than an inner diameter of the internal passage of the second tubular region. The oocyte retrieval needle is a double lumen needle.

29 Claims, 10 Drawing Sheets

(51) Int. Cl.
  *A61B 17/425* (2006.01)
  *A61B 10/04* (2006.01)
(58) Field of Classification Search
  USPC .................................................. 600/33–35
  See application file for complete search history.

(56) References Cited

U.S. PATENT DOCUMENTS

| | | | |
|---|---|---|---|
| 3,995,631 A | 12/1976 | Higuchi et al. | |
| 4,134,402 A | 1/1979 | Mahurkar | |
| 4,493,696 A | 1/1985 | Uldall | |
| 4,653,475 A * | 3/1987 | Seike | A61D 19/04 600/104 |
| 4,810,244 A * | 3/1989 | Allen | A61B 17/3415 604/164.11 |
| 4,824,434 A * | 4/1989 | Seitz, Jr. | A61B 17/435 600/33 |
| 4,846,785 A * | 7/1989 | Cassou | A61D 19/04 600/34 |
| 4,909,800 A | 3/1990 | Gross | |
| 5,160,319 A * | 11/1992 | Emery | A61B 17/435 604/158 |
| 5,360,389 A | 11/1994 | Chenette | |
| 5,484,399 A | 1/1996 | DiResta | |
| 5,827,174 A * | 10/1998 | Reuss, Jr. | A61B 17/435 600/33 |
| 5,843,023 A * | 12/1998 | Cecchi | A61B 17/435 604/44 |
| 5,902,279 A | 5/1999 | Powles et al. | |
| 6,033,358 A | 3/2000 | Mers Kelly et al. | |
| 6,193,647 B1 | 2/2001 | Beebe et al. | |
| 6,306,132 B1 | 10/2001 | Moorman et al. | |
| 6,461,302 B1 | 10/2002 | Thompson | |
| 6,511,415 B1 * | 1/2003 | Christine | A61B 17/43 600/35 |
| 6,527,752 B1 * | 3/2003 | Bosley, Jr. | A61B 17/43 604/264 |
| 6,593,129 B1 * | 7/2003 | Takeshita | C12M 23/50 435/285.1 |
| 6,607,503 B1 | 8/2003 | Berbers | |
| 6,929,598 B2 | 8/2005 | Kaneko | |
| 6,929,623 B2 | 8/2005 | Stone | |
| 6,979,339 B2 | 12/2005 | Bishop | |
| 8,092,481 B2 | 1/2012 | Nance et al. | |
| 2003/0069541 A1 | 4/2003 | Gillis et al. | |
| 2003/0083672 A1 * | 5/2003 | Bishop | A61B 17/435 606/119 |
| 2004/0092791 A1 * | 5/2004 | Bateman | A61B 17/435 600/34 |
| 2004/0225180 A1 * | 11/2004 | Junger | A61B 17/435 600/33 |
| 2005/0137525 A1 * | 6/2005 | Wang | A61M 37/0015 604/93.01 |
| 2005/0143619 A1 * | 6/2005 | Spittle | A61B 17/435 600/33 |
| 2005/0177117 A1 | 8/2005 | Crocker et al. | |
| 2005/0239040 A1 | 10/2005 | Lindenberg | |
| 2006/0078961 A1 * | 4/2006 | Chiu | B01L 3/0293 435/29 |
| 2006/0135915 A1 * | 6/2006 | Tucker | A61B 17/3401 604/264 |
| 2006/0183973 A1 | 8/2006 | Kamrava | |
| 2006/0205073 A1 * | 9/2006 | Oktay | A61B 17/435 435/366 |
| 2006/0206055 A1 | 9/2006 | Ice | |
| 2006/0276759 A1 | 12/2006 | Kinast et al. | |
| 2008/0058595 A1 * | 3/2008 | Snoke | A61B 1/00135 600/114 |
| 2008/0091119 A1 * | 4/2008 | Moffitt | A61B 10/0045 600/551 |
| 2008/0213899 A1 * | 9/2008 | Olgac | C12M 21/06 435/455 |
| 2008/0243031 A1 | 10/2008 | Seibel | |
| 2012/0309043 A1 | 12/2012 | Ramsing et al. | |

FOREIGN PATENT DOCUMENTS

| | | |
|---|---|---|
| EP | 1967147 A2 | 9/2008 |
| JP | 62064344 A | 3/1987 |
| JP | 64-907 U | 1/1989 |
| JP | 64-3605 U | 4/1989 |
| JP | 198954058 B | 11/1989 |
| JP | 07-22716 U | 4/1995 |
| JP | 08336595 A | 12/1996 |
| JP | 10099353 A | 4/1998 |
| JP | 2954287 B | 9/1999 |
| JP | 2001190560 A | 7/2001 |
| JP | 2003126106 A | 5/2003 |
| JP | 2005177237 A | 7/2005 |
| JP | 2007159657 A | 6/2007 |
| JP | 2006055219 A | 3/2016 |
| SU | 1750679 A1 | 7/1992 |
| WO | 2004089229 A1 | 10/2004 |
| WO | 2005025434 A1 | 3/2005 |
| WO | 2009150399 A1 | 12/2009 |

OTHER PUBLICATIONS

Aziz, et al. "Effect of aspirating needle calibre on outcome of in-vitro fertilization." Human Reproduction, vol. 8, No. 7 (1993), pp. 1098-1100, abstract only.

Awonuga, et al. "A prospective randomized study comparing needles of different diameters for transvaginal ultrasound-directed follicle aspiration." Fertility and Sterility, vol. 65, No. 1 (1996), pp. 109-113, abstract only.

Bols, et al. "Effects of aspiration vacuum and needle diameter on cumulus oocyte complex morphology and developmental capacity of bovine oocytes." Theriogenology, vol. 45, No. 5 (1996), pp. 1001-1014.

Bols, et al. "Effects of needle tip bevel and aspiration procedure on the morphology and developmental capacity of bovine compact cumulus oocyte complexes." Theriogenology, vol. 47, No. 6 (1997), pp. 1221-1236.

Wikland, et al. "A randomized controlled study comparing pain experience between a newly designed needle with a thin tip and a standard needle for oocyte aspiration." Human Reproduction, vol. 26, No. 6 (2011), pp. 1377-1383.

Wikland, et al. "Pain experience during oocyte aspiration: comparison between a newly designed reduced needle and a standard needle." 26th Annual Meeting of the European-Society-of-Human-Reproduction-and-Embryology. vol. 25, Suppl. 1, No. O-226, Oxford University Press (2010).

Bols, "Transvaginal ovum pick-up in the cow: technical and biological modifications." Merelbeke: Universidade de Gent (1997), Ph.D. Thesis; 207 pages.

Meintjes, et al. "Transvaginal aspiration of oocytes from hormone-treated pregnant beef cattle for in vitro fertilization." Journal of Animal Science, vol. 73, No. 4 (1995), pp. 967-974.

Boni, "Ovum pick-up in cattle—a 25-yr retrospective analysis." Anim. Reprod., vol. 9, No. 3 (2012), pp. 362-369.

Čech, et al., "Limitations of ultrasound guided follicular aspiration for analysis of ovarian follicular fluid in dairy cattle." Acta Veterinaria Brno, vol. 80, No. 2 (2011), pp. 179-184, and "Plate I".

Institute of Food and Agricultural Sciences, University of Florida, "Cow Reproductive Tract Anatomy," available at animal.ifas.ufl.edu/ans3319/lab.../lab_1d_female_reproductive%20_anatomy.pdf, accessed Sep. 14, 2016, pp. 1-23.

Parker, et. al., "Reproductive tract anatomy and physiology of the cow: Guide B-212," Cooperative Extension Service, College of Agriculture and Home Economics. 2002. p. 1-5.

Prange, et al., "Anatomy of the Cow's Reproductive Tract," Cooperative Extension Service, 2007, pp. 1-5.

(56) References Cited

OTHER PUBLICATIONS

Mathis, et al. "Reproductive Tract Anatomy and Physiology of the Cow," Western Beef Resource Committee, Cattle Producer's Library, Reproductions Section, Cooperative Extension Service, 2008, pp. 440-1 to 440-4.

Freudenrich, "How Plastics Work: Types of Plastics," 2016, available at http://science.howstuffworks.com/plastic4.htm; accessed Sep. 20, 2016, pp. 1-6.

FreelinWade, "Polyethylene Tubing," available at http://www.freelin-wade.com/polyethylene-tube.html; accessed Sep. 20, 2016, pp. 1-2.

Miller, "A new follicle aspiration needle set is equally effective and as well tolerated as the standard needle when used in a prospective randomized trial in a large in vitro fertilization program," Fertility and Sterility, vol. 81 (2004), pp. 191-193.

Russian Decision on Granting issued in related Application No. 2009134720/14(048900) dated Apr. 24, 2012, 4 pages (listing references cited by ROSPATENT).

International search report of PCT/GB2008/000251, dated May 14, 2008.

* cited by examiner

PRIOR ART

PRIOR ART

PRIOR ART

PRIOR ART

SAMPLING NEEDLE

CROSS-REFERENCE TO RELATED APPLICATIONS

This application is a continuation of U.S. application Ser. No. 12/532,362, filed Jan. 20, 2010, which is a national stage application of International Appl. PCT/GB2008/000251, filed Jan. 24, 2008, which claims priority of United Kingdom Patent Application GB0719037.4, filed Sep. 28, 2007, all of which are hereby incorporated by reference.

FIELD OF THE INVENTION

The invention relates to a sampling needle, in particular to a needle suitable for oocyte retrieval from a human or animal subject. The invention also relates to a method of retrieving a sample, in particular an oocyte, from a human or animal subject.

BACKGROUND OF THE INVENTION

In Vitro Fertilization (IVF) is a common intervention to assist couples suffering from childlessness. The first step in an IVF cycle, after any required hormonal stimulation of a female subject, is the retrieval, or aspiration, of oocytes. Hormone stimulation leads to an increased number of follicles being matured in the female. In a normal menstrual cycle, one to two oocytes are produced. In contrast, about 5 to 15 oocytes are generally matured in a successful IVF cycle. Today there is an increasing interest in using no or minimal hormone stimulation and instead to mature the oocytes after retrieval or to use a natural cycle in which the normally one or two matured oocytes are considered sufficient for the IVF procedure.

Independent of the method of hormone stimulation, each oocyte resides in a follicle. During an IVF procedure the follicles are emptied while still in the ovaries. This is normally done transvaginally which means that an oocyte retrieval needle is used to penetrate the vaginal wall and the ovaries. Following localization of the follicles by ultrasound, an oocyte retrieval needle is used to puncture and enter each follicle and then the follicular fluid containing the oocytes is retrieved by aspiration. The retrieval is achieved through an induced negative pressure. In cases where the oocytes are not released from the follicle through aspiration only, a pre-warmed flush solution may be used together with the aspiration to release the oocytes and to increase the aspirated fluid volume.

Oocyte retrieval needles used to empty follicles in vivo for the purpose of an IVF cycle may comprise a single or double lumen. Double lumen needles have a first lumen for retrieving oocytes from a follicle and a second lumen for concurrently flushing media into the follicle. This is believed, by some, to release oocytes from the follicle better than retrieval with a single lumen needle without flushing. However, it is more common to use a single lumen needle without flushing. Although a single lumen needle could be used to both retrieve and flush, it is not possible to use a single lumen needle to flush and aspirate at the same time. Therefore, when using a single lumen needle with flushing, there is a risk that the oocytes are flushed away instead of retrieved.

Oocyte retrieval needles marketed today are of uniform outer diameter (OD) and inner diameter (ID) along the full length of the needle. The most common needles are either 16 or 17 Gauge which correspond to an OD of 1.65 mm and 1.47 mm respectively. These needles are available from for example Cook Medical Inc. (Bloomington, Ind., USA), Smiths Medical International (Watford, UK) and Gynetics Medical Products N.V. (Achel, Belgium). Needles of 18 Gauge (1.27 mm OD) are available from Smiths Medical International.

The length of an oocyte retrieval needle varies, for example, depending on the type of needle guide used which in turn depends on the type of ultrasound transducer used. Typical total needle lengths are between 200 mm and 400 mm.

The inner diameter (ID), i.e. luminal diameter, of the oocyte retrieval needle must be larger than the diameter of the oocyte, which for a human is approximately 0.1 to 0.2 mm. The ID of the needle should also allow movement of the cumulus cell mass covering the oocytes. Production and material restraints affect how small the ID can be, as do the stress and friction induced on the oocytes within a thin needle.

The retrieval procedure normally takes about 10 to 30 minutes, mainly depending on how many follicles there are to penetrate and empty. Without anesthesia and sedation it is a rather difficult and, in some cases, very painful procedure for the female. Therefore it is standard in some countries to use general anesthesia during the procedure. However, the use of general anesthesia is associated with medical risks and the requirement of having an anesthetist present increases costs. Consequently, some countries, such as those in Scandinavia, perform oocyte retrieval under mild sedation and/or local anesthesia. The trend today is that more and more clinics are moving towards using mild sedation and/or local anesthesia as it is less costly and safer, although it creates more discomfort or pain for the female.

Needle manufacturers have responded to this change in procedure by producing thinner oocyte retrieval needles in order to cause less pain to the patient. A relationship has been found between the thickness of the needle and the pain felt by a subject (Aziz et al (1993) Human Reproduction 8(7):1098-1100). This study compared the use of two needle diameters: 16 and 18 gauge. A 16 gauge needle was used in one ovary and an 18 gauge needle was used in the other ovary. Use of a different needle in each ovary allowed the subject to be used as her own control. Mild sedation was used on the subjects and the pain was self assessed on a 0 to 5 scale. It was found that the thinner needle was significantly associated with less perceived pain.

Perceived pain and cramps are also problems following the oocyte retrieval procedure. In a study by Miller et al (2004) (Fertility and Sterility 81(1):191-193), self assessed pain and cramping was scored 30 minutes and 24 hours after the oocyte retrieval. This showed that there was pain and cramping both at 30 minutes and during the 24 hours following oocyte aspiration. There is no data at this time to confirm that pain and cramps after the aspiration procedure are actually reduced with a thinner needle, but as less tissue damage occurs with a thinner needle, this would be expected.

As mentioned above, thinner needles cause less trauma and bleeding than thicker needles. This is advantageous because trauma and bleeding may affect the implantation of the embryo. Implantation is generally carried out only two to six days after the retrieval of the oocyte, therefore any trauma caused during the retrieval process might prevent proper implantation.

However, the use of thinner needles also has several disadvantages as a thinner needle also has a narrower lumen. For example, the sample, e.g. an oocyte, might get stuck and/or harmed within the lumen of the thin needle. The approximate diameter of a human oocyte is 0.1 to 0.2 mm and, with the cumulus cells surrounding the oocyte, the whole cell mass can have a diameter as large as 10 mm (Aziz et al 1993). Therefore, the thinner the needle, the larger is the risk of damaging an oocyte as it travels through the needle. Consequently the use of a thinner needle increases the risk of harming the oocytes which could reduce the likelihood of an IVF procedure resulting in a successful pregnancy.

Another disadvantage of thinner needles is that, for application of a given negative pressure, aspiration through a thinner needle takes a longer time than through a thicker needle. The longer the sample (e.g. oocyte and follicular fluid) is in the needle, the longer it is subjected to room temperature and thus the sample cools down more. A thinner needle lumen also increases the contact area between the needle wall and the sample, which further cools down the sample. Some samples, e.g. oocytes, are very sensitive to temperatures below physiological temperature and lose viability as temperature drops.

An alternative to the longer aspiration time required for a thinner needle would be to increase the applied negative pressure to speed up movement of the follicular fluid through the needle. However, this has the disadvantage that the application of a higher pressure may stress and cause other physical damage to the sample. Application of too high a negative pressure is a common concern during oocyte aspiration as it might harm the zona pellucida of the oocyte. Also, an applied negative pressure can never exceed 1 atm (101.3 kPa), when working in a normal pressure environment. Furthermore, a thin needle also has the disadvantage of being more difficult for a user to manipulate as it is more likely to bend than a thicker needle.

Current oocyte retrieval needles will be discussed in relation to the following drawings FIGS. 1 to 5, in which, for ease of reference, like parts have been referred to by like reference numbers. Data providing results of comparisons of needles according to the present invention and other needles are given in FIGS. 6 to 10.

FIG. 1 is a schematic longitudinal cross section of a uterus and apparatus for ultrasound guided transvaginal aspiration of follicles from an ovary (prior art);

FIG. 2 is a schematic longitudinal cross section of a single lumen needle suitable for use with the apparatus shown in FIG. 1 (prior art);

FIG. 3 is a longitudinal cross section of a double lumen needle suitable for use with the apparatus shown in FIG. 1 (prior art);

FIG. 4 is a longitudinal cross section of a single lumen needle connected to a syringe, the single lumen needle being suitable for transvaginal aspiration of follicles from an ovary (prior art); and FIG. 5 is a longitudinal cross section of a single lumen needle connected to a syringe via tubing, the single lumen needle being suitable for transvaginal aspiration of follicles from an ovary (prior art).

FIG. 1 shows a uterus (150) comprising the fundus (152), myometrium (154), vagina (156), fallopian tubes (160), ovaries (158) and ovarian follicles (104). Typical known apparatus (100) for ultrasound guided transvaginal aspiration of an ovarian follicle (104) is shown in situ. A single lumen oocyte retrieval needle (102) is introduced transvaginally into an ovarian follicle (104) containing the oocyte and is held on a needle guide (106) which in turn is held on an ultrasound transducer (108). The ultrasound transducer produces an ultrasound visual field of the follicles (109). The trailing end of the single lumen needle is connected to aspiration tubing (110) which in turn is connected to a test tube (112) for collection of follicular fluid containing the oocytes. A negative pressure is induced in the test tube (112) by application of a vacuum pump (not shown). The test tube (112) is sealed with a silicone stopper (114) with connectors (not shown).

The oocyte retrieval needle (102) may be a single lumen needle or a double lumen needle. A single lumen needle is shown in FIG. 2. A double lumen needle is shown in FIG. 3. Other aspiration needle configurations, each with a Luer connector and a syringe to induce negative pressure, are shown in FIGS. 4 and 5.

FIG. 2 shows a known single lumen needle apparatus (200) which comprises an oocyte retrieval needle (202). The trailing end of the needle (202) comprises a fingertip grip (222). The trailing end of the needle (202) is connected to aspiration tubing (210) which, in turn, is connected to a test tube (212) via a silicone stopper (214). The test tube (212) is connected to a vacuum pump (not shown), via the silicone stopper (214), a Luer connection (216) and vacuum tubing (218). Application of a vacuum to the vacuum tubing (218) causes fluid to be drawn into the needle (202) and consequently into the test tube (212) in the direction of arrow A.

FIG. 3 shows a known double lumen needle apparatus (300). The trailing end of the oocyte retrieval needle (302) comprises a fingertip grip (322). The trailing end of the needle (302) is connected to flush tubing (324). The distal end of the flush tubing (324) comprises a Luer connection (325) for connection to a source of flush media. The trailing end of the needle (302) is also connected to aspiration tubing (310) which in turn is connected to a test tube (312) for collection of the follicular fluid containing the oocytes. A negative pressure is induced in the test tube (312) by application of vacuum pump (not shown). The test tube (312) is connected to the vacuum pump (not shown), via a silicone stopper (314), a Luer connection (316) and vacuum tubing (318). Application of a vacuum to the aspiration tubing (318) causes fluid to be drawn into the needle (302) and consequently into the test tube (312) in the direction of arrow A. Flushing media may be flushed through the flushing tubing (324) into the needle (302) in the direction of arrow B.

FIG. 4 shows another known single lumen needle apparatus (400), which comprises, at the trailing end of the oocyte retrieval needle (402), a fingertip grip (422). The trailing end of the needle (402) is connected to a syringe (426) via a Luer connection (not shown). Withdrawal of the syringe plunger (428) from the syringe barrel (430) induces a negative pressure within the needle (402) and causes fluid to be drawn into the needle (402) and consequently into the syringe (426) in the direction of arrow A.

FIG. 5 shows a known alternative to the needle apparatus of FIG. 4. A single lumen needle apparatus (500) comprises a single lumen oocyte retrieval needle (502), at the trailing end of which is a fingertip grip (522). The trailing end of the needle (502) is connected to a syringe (526) via aspiration tubing (524) and a Luer connection (not shown). Withdrawal of the syringe plunger (528) from the syringe barrel (530) induces a negative pressure within the needle (502) and causes fluid to be drawn into the needle (502) and consequently into the syringe (526) in the direction of arrow A.

Previous inventions relating to needles include those described in WP2005/025434, US2005/0143619, U.S. Pat. No. 5,843,023, U.S. Ser. No. 6,979,339, U.S. Pat. No. 6,461,302 and U.S. Pat. No. 6,929,623. The needles described in WO2005/025434, US2005/0143619, U.S. Pat. No. 5,843,023, U.S. Ser. No. 6,979,339 and U.S. Pat. No.

6,461,302 are all constructed with uniform diameters. As such they either impose pain and/or tissue trauma on the female or they may induce stress and/or trauma to the oocyte. The use of a needle with a large inner diameter has an advantage in that it minimizes stress and/or trauma induced on the sample, e.g. oocyte, being retrieved and it works fast. Use of a needle with a small inner diameter has a disadvantage in that it results in a long retrieval, i.e. aspiration, time. A long retrieval time is inconvenient for the doctor carrying out the aspiration, inconvenient and uncomfortable for the subject from which the sample is being retrieved and increases the extent to which the sample cools and/or is otherwise stressed or traumatized during the retrieval procedure.

WO2005/025434 discloses an anesthetic needle for internal periovarial blocking in conjunction with egg retrieval.

US2005/0143619 discloses an ovum collection device comprising a handle, a collection needle extending from the handle and heating arrangement to maintain the collection needle at a selected temperature to prevent damage to the ovum being collected. Although this invention might solve the temperature issue during oocyte aspiration, it discloses a needle of uniform diameter and as such it has either the disadvantages of a needle with a small ID or a needle with a large OD, as discussed above.

U.S. Pat. No. 5,843,023 and U.S. Pat. No. 6,979,339 both disclose aspiration needle constructions with side ports. Both U.S. Pat. No. 5,843,023 and U.S. Pat. No. 6,979,339 disclose even sized needles that either has the disadvantages of a needle with a small ID or a needle with a large OD, as discussed above.

U.S. Pat. No. 6,461,302 discloses an ovum retrieval device for retrieving an ovum and follicular fluid from a follicle. The device comprises a needle connected to a means for inducing suction on the needle and therefore allowing a sample to be drawn into the needle.

U.S. Pat. No. 6,929,623 discloses a syringe comprising a needle having a first region with a wide diameter connected to a second region with a narrow diameter. The needle is used for delivery of, rather than for retrieval of, robust viscous liquids to ducts, such as the urethra, esophagus and blood vessels of a patient. There is no suggestion to use the needle to collect samples such as oocytes.

SUMMARY OF THE INVENTION

The present invention provides a sampling needle which retains the advantages of a thin needle whilst reducing and/or eliminating disadvantages associated with a thick needle. Thus the invention provides a needle suitable for retrieval of a biological sample from a subject, in particular a sample which is located in a position which is difficult to access such as a location which requires a body cavity to be traversed before a tissue can be accessed and penetrated. For example, the biological sample may be an oocyte. The biological sample may be a viscous liquid or may be present in a viscous liquid. For retrieval of an oocyte with a needle, the needle must traverse the vagina before the ovary and ovarian follicle can be penetrated. The sampling needle may be a surgical or medical needle.

Accordingly, a first aspect of the invention provides a sampling needle comprising a first (leading) tubular region in fluid communication with a second (trailing) tubular region, the first tubular region comprising a leading end for penetrating the tissue of a subject and the second tubular region comprising a trailing end for fluid communication with a means for receiving a fluid in which the first tubular region has an outer diameter and inner diameter which is less than the outer and inner diameter of the second tubular region and the first tubular region has an inner diameter which is smaller than the inner diameter of the second tubular region.

An advantage of the sampling needle according to the present invention is that only the relatively thin first tubular region invades the tissue from which the sample is being retrieved whereas the relatively wide second tubular region does not invade the tissue.

The first and second tubular regions may be arranged along a common central axis running through the lumen of both the first and second tubular regions. Alternatively, the first and second tubular regions may be arranged off center relative to each other, i.e. the needle is asymmetrical around a central axis running through the lumen of both the first and second tubular regions.

The first tubular region may be connected to the second tubular region via a tapered region. The tapered region may provide a gradual change in diameter between the first tubular region and the second tubular region. The tapered region may be steep or shallow. Alternatively, a tapered region may not be present and the connection between the first and second tubular regions may be substantially right angled.

The first tubular region may itself be tapered. Preferably the taper is from a relatively narrow leading end to a wider region which connects the first tubular region to the second tubular region.

Preferably the means for receiving a fluid is suitable for receiving a biological sample. The means for receiving a fluid is preferably capable of being sealed. Preferably the means for receiving a fluid is sterile. The means for receiving a fluid may be any suitable vessel including a test tube.

For a human oocyte retrieval procedure the outer diameter of the first tubular region is preferably from 0.6 mm to 1.2 mm, more preferably from 0.8 mm to 1.0 mm, most preferably about 0.9 mm.

For a human oocyte retrieval procedure, the outer diameter of the second tubular region is preferably greater than or equal to 1.1 mm, more preferably greater than or equal to 1.2 mm, most preferably greater than or equal to 1.4 mm.

For a human oocyte retrieval procedure, the inner diameter of the first tubular region is preferably greater than or equal to about 0.2 mm, more preferably greater than or equal to about 0.4 mm, most preferably greater than or equal to about 0.6 mm. The inner diameter of the first tubular region of an oocyte retrieval needle should always be at least as large as the diameter of the oocyte from the specific species it is being retrieved from. If the sample is not an oocyte, the inner diameter should be at least as large as the diameter of the vulnerable part of the sample being retrieved.

For a human oocyte retrieval procedure, the inner diameter of the second tubular region is preferably greater than or equal to about 0.9 mm, more preferably greater than or equal to about 1.1 mm, most preferably greater than or equal to about 1.2 mm.

In use, the leading end of the needle penetrates the tissue of the subject whilst the trailing end does not penetrate the tissue of the subject. In use, the leading end of the needle may penetrate one or more of the vaginal wall, an ovary and a follicle of a subject, such as a patient. An advantage of the sampling needle of the invention is that the leading region of the needle, which has a relatively small outer diameter, may inflict less pain, and/or less trauma and/or less tissue damage on a subject than a needle having a leading region having a larger outer diameter. An advantage of the trailing region having a larger inner diameter than the leading region is that it allows faster flow of material, under equal negative pressure, within the trailing region and therefore works faster and may confer less stress on a sample, e.g. oocyte, being retrieved. Thus the large inner diameter of the second tubular region means that it serves as a good transport channel.

The first tubular region is preferably at least as long as the anatomical distance that must be penetrated in order to reach the site of the sample to be retrieved. The site of the sample may be a tissue. For example, for oocyte retrieval, the first tubular region is preferably sufficiently long to reach the follicles in the ovaries through the vaginal wall. For use in a human subject the first tubular region is at least 30 mm long, more preferably at least 40 mm long. The first tubular region may be from 30 to 80 mm long, for example 30, 35, 40, 45, 50, 55, 60, 65, 70, 75 or 80 mm long. The first tubular region of the needle can be longer than required to reach the site of the sample, however, as the length of the first tubular region increases, the advantages associated with the larger diameter of the second tubular region decrease. The longer the thin part of the needle is, the longer time the oocytes spend in the needle and the more they will cool down during the procedure and the more friction and, potentially, stress is induced on the oocytes.

The total length of the first and second tubular regions of the needle must be sufficiently long to reach the sample. For an oocyte retrieval needle, the total required length depends on the anatomical size and construction of the female subject. That is, the second (trailing) tubular region must be sufficiently long to traverse the vagina. The first (leading) tubular region must be sufficiently long to penetrate the site, e.g. tissue, in which the sample is located, for example an ovary, particularly a follicle of an ovary, and contact the sample without the second (trailing) tubular region penetrating the site, e.g. tissue. Contacting the sample allows retrieval of the sample from the site. For a human subject it is preferred that the first and second tubular regions have a combined length of from 150 mm to 500 mm. For example, the first and second tubular regions may have a combined length of from 200 mm to 400 mm, for example 300 mm.

It is particularly preferred that the length of the first tubular region is sufficiently long to contact the sample without the second tubular penetrating the site of the sample, e.g. tissue. Preferably the first tubular region is not excessively long to ensure that the sample is not exposed to unnecessary stress. For a human oocyte retrieval needle the first tubular region should preferably be greater than or equal to about 30 mm, more preferably greater than or equal to about 40 mm and preferably no longer than 100 mm, more preferably no longer that 80 mm and most preferably no longer than 60 mm.

The length of the second tubular region depends on the anatomy of the subject, i.e. the length is sufficiently long to reach the sample and on the equipment required to stabilize the needle and/or to visualize the sample. Suitable dimensions of the sampling needle vary depending on the sample to be retrieved and the subject from which the sample is to be retrieved. For example, oocytes of some animals are larger than human oocytes. Oocytes of other animals are smaller than human oocytes. Therefore, the sample and subject determine suitable dimensions for the inner and outer diameter of the first and second tubular regions. Likewise, different animals have different anatomical constructions. For example, an animal may have a body cavity, such as a vagina, which is longer or shorter to traverse than that of a human. Likewise, the sample, such as an oocyte, may be located at a shallower or deeper depth within the site, such as an ovary or ovarian follicle, compared with a human. Furthermore, anatomical dimensions show natural variation within a species, for example due to variations in height, mass and body mass index. The subject may be a human, or an animal such as a cow, a sow, a dog, a horse, a mouse, an elephant or a giraffe. Using knowledge of anatomy, the skilled person is able to select suitable dimensions for the sampling needle.

Preferably, the configuration of the needle is such that the sample retrieval time is sufficiently short to maintain an acceptable aspiration time meaning an aspiration time which for practical purposes is comparable to the aspiration time required when using a standard needle, e.g. a needle with a uniform outer diameter of 1.4 mm, a uniform inner diameter of 1.0 mm and a length of 355 mm. The aspiration time of a sample is dependent upon the negative pressure applied, the viscosity of the sample being aspirated and the volume of the sample being aspirated. A comparable aspiration time is one which is as low as the aspiration time with a standard needle, lower than the aspiration time with a standard needle or up to 30% longer, preferably no more than 20% longer, than the aspiration time with a standard needle. A standard needle is, for example, a needle having a uniform inner diameter of 1.0 mm and a uniform outer diameter of 1.4 mm and, for example, having a length of 355 mm. An acceptably short aspiration time is one which minimizes cooling of the sample during retrieval, minimizes the time during which a doctor needs to be present, minimizes the time during which the subject experiences discomfort during retrieval and minimizes damage and/or trauma to the sample being retrieved. The aspiration time may be less than two minutes, for example less than one minute. The sample being retrieved may have a volume of from 3 ml to 8 ml, for example 4 or 5 ml. A negative pressure of up to 1 atmosphere (i.e. from 0 to 101.3 kPa) may be applied to the trailing end of the needle.

The sampling needle may be formed from one or more materials selected from stainless steel, carbon fibre, hard plastics, ceramic and glass. Particularly preferred materials include a stainless steel selected from AISI 304, AISI 316, SIS 2346 and SIS 2543. The most preferred material is AISI 304 stainless steel. The first and second tubular regions may be made from the same or from different materials.

Preferably the needle comprises a sharp tip. The tip may be adapted to improve visibility under ultrasound. The tip may be echogenic. For example, the external surface of the tip of the needle may be provided with one or more grooves.

The sampling needle may be formed from a single piece of material or may be formed from two or more pieces of material joined together to form a single tube.

The sampling needle of the present invention may be fitted to or with one or more of an ultrasound transducer, a vacuum pump, aspiration tubing, flushing tubing, a collection tube, a stopper for the collection tube, a vacuum pump, a syringe, a needle guide, a fingertip grip and connectors for connecting the tubing to one or more of the collection tube, vacuum pump and syringe such as those described in relation to FIGS. 1 to 5. The tubing may comprise TEFLON (R). Furthermore, the sampling needle of the present invention may be used in a single lumen or double lumen needle apparatus such as those described in relation to FIGS. 1 to 5. For example, the apparatus may comprise one or more of the components described in relation to FIGS. 1 to 5.

A second aspect of the invention provides a method of harvesting a sample from a subject comprising inserting a sampling needle in accordance with the invention into the subject, as described above, and withdrawing the sample from the subject. Preferably the sample is an oocyte. Preferably the subject is a human. Alternatively, the subject may be an animal such as a cow, a sow, a dog, a horse, a mouse, an elephant or a giraffe.

Preferably only the first (leading) tubular region of the sampling needle penetrates the tissue of the subject. That is, preferably the second (trailing) region of the sampling needle does not penetrate the tissue of the subject. This has the advantage that only the narrow part, i.e. the first tubular region, of the needle penetrates the tissue of the subject and this may minimize the pain, discomfort and trauma experienced by the subject. For example, about 30 mm or about 40 mm of the first tubular region may be inserted into the subject during a human oocyte retrieval procedure.

A third aspect of the invention provides the use of a sampling needle, as described above, in a method of harvesting a sample from a subject. The subject may be a human or an animal such as a cow, a sow, a dog, a horse, a mouse, an elephant or a giraffe. The sample may be situated at a distance from the location at which the needle invasively enters the site, e.g. tissue, containing the sample. The sample may be an oocyte.

Figure 1:
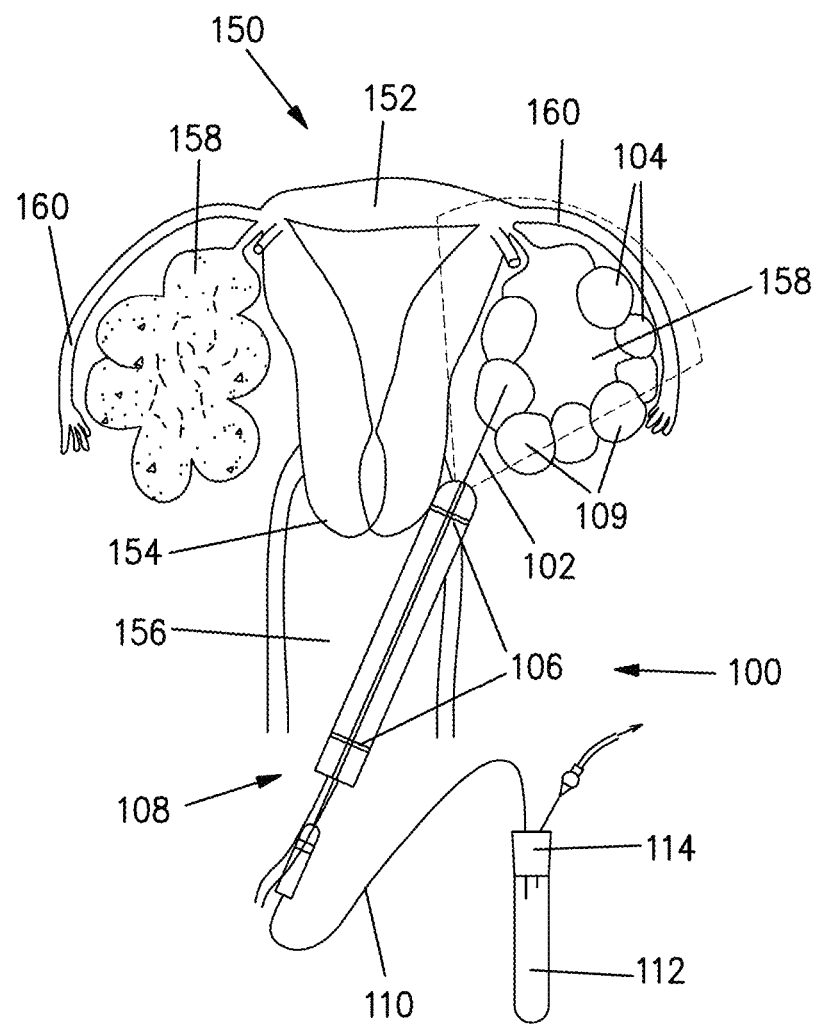
FIG. 1 is a schematic longitudinal cross section of a uterus and apparatus for ultrasound guided transvaginal aspiration of follicles from an ovary (prior art)
Figure 2:
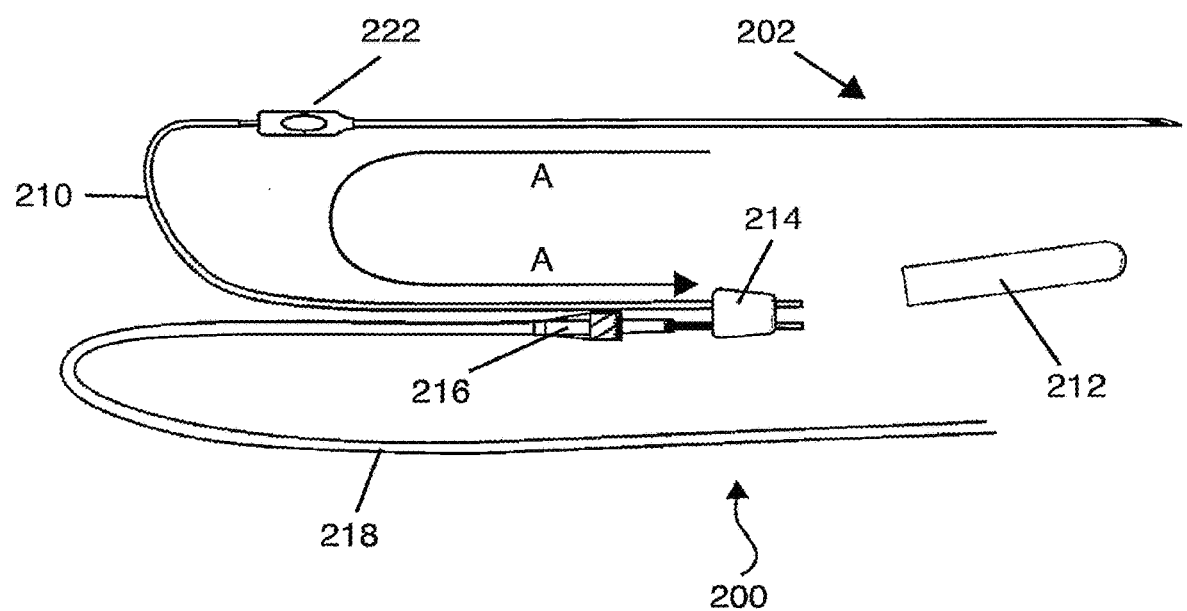
FIG. 2 is a schematic longitudinal cross section of a single lumen needle suitable for use with the apparatus shown in FIG. 1 (prior art)
Figure 3:
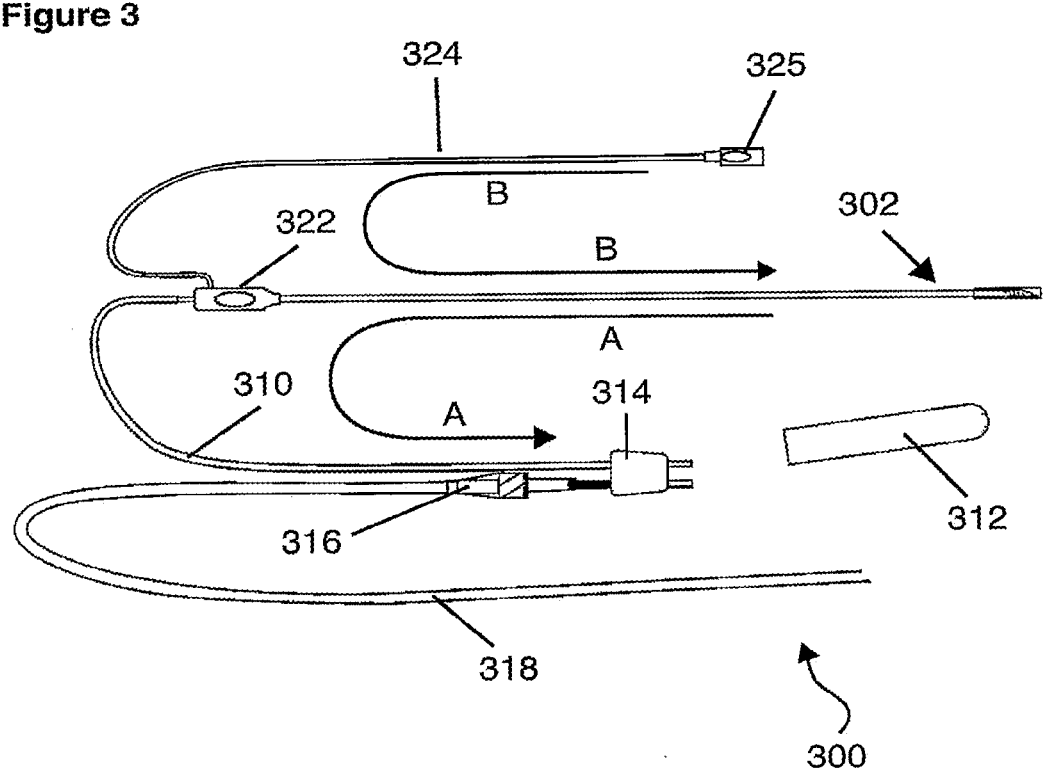
FIG. 3 is a longitudinal cross section of a double lumen needle suitable for use with the apparatus shown in FIG. 1 (prior art)
Figure 4:
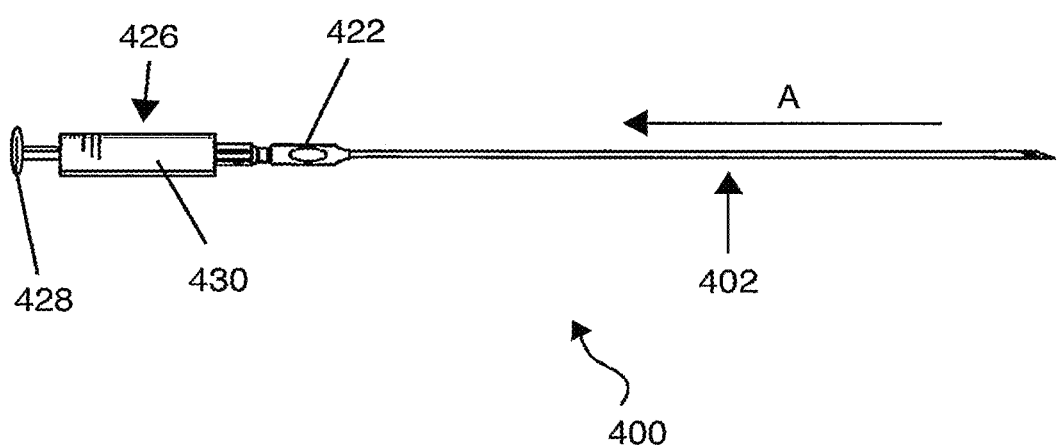
FIG. 4 is a longitudinal cross section of a single lumen needle connected to a syringe, the single lumen needle being suitable for transvaginal aspiration of follicles from an ovary (prior art)
Figure 5:
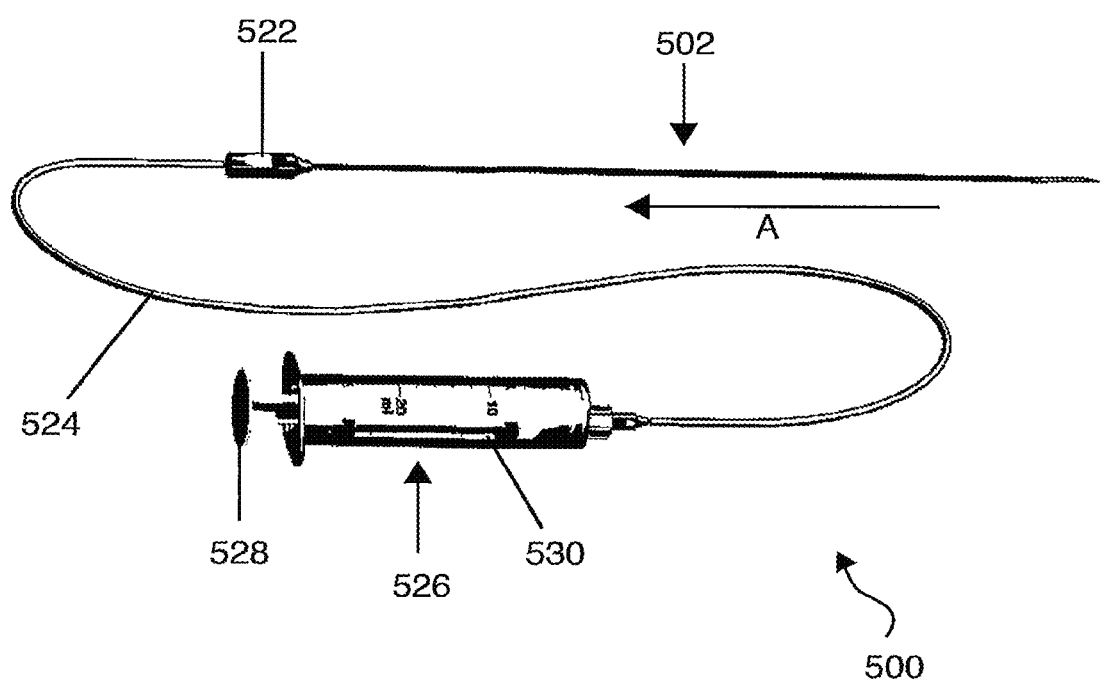
FIG. 5 is a longitudinal cross section of a single lumen needle connected to a syringe via tubing, the single lumen needle being suitable for transvaginal aspiration of follicles from an ovary (prior art).
Figure 6:
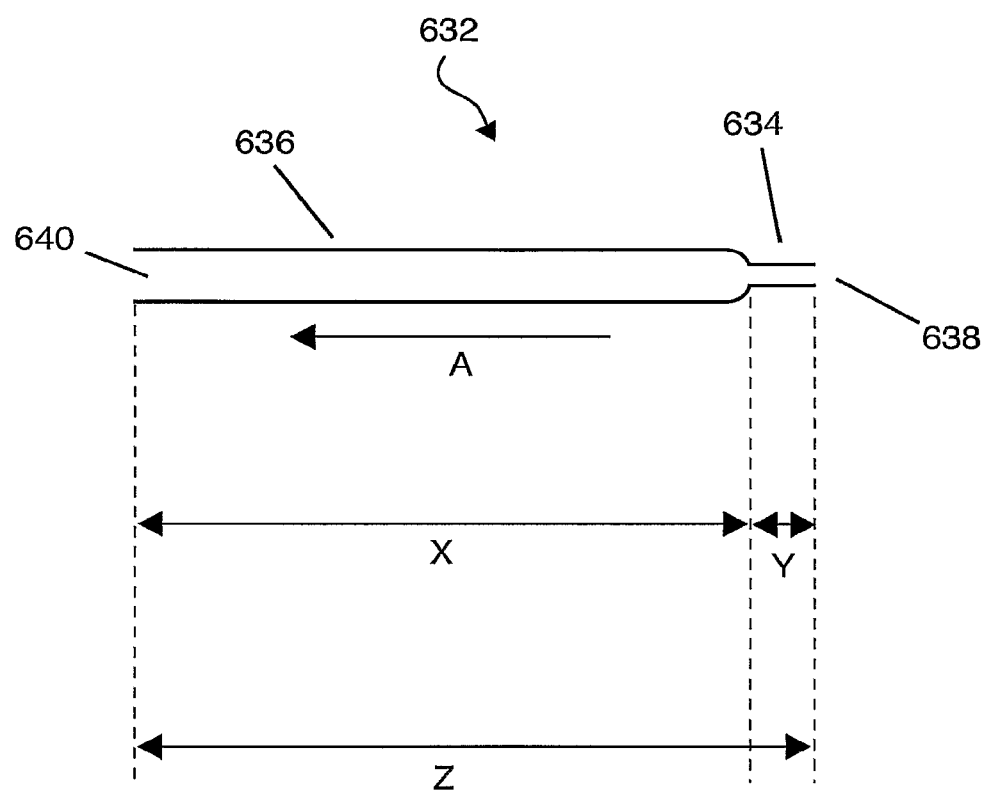
Figure 7:
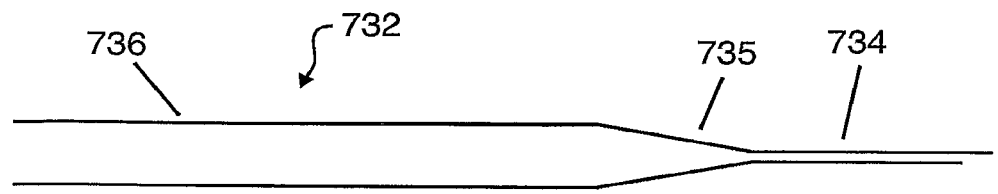
Figure 8:
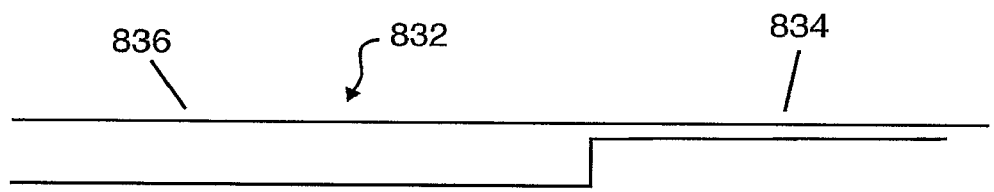
Figure 9:
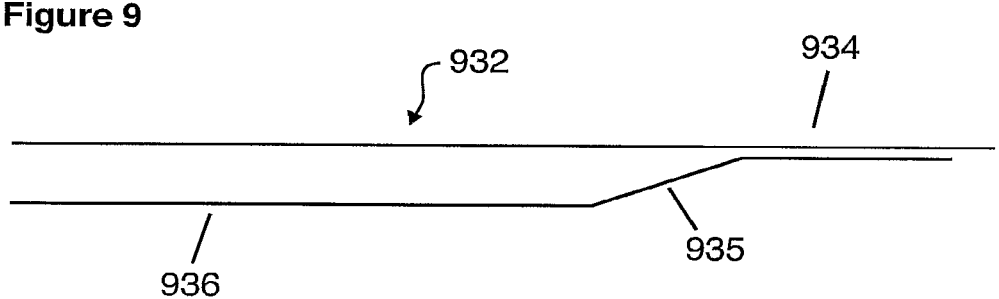
Figure 10:
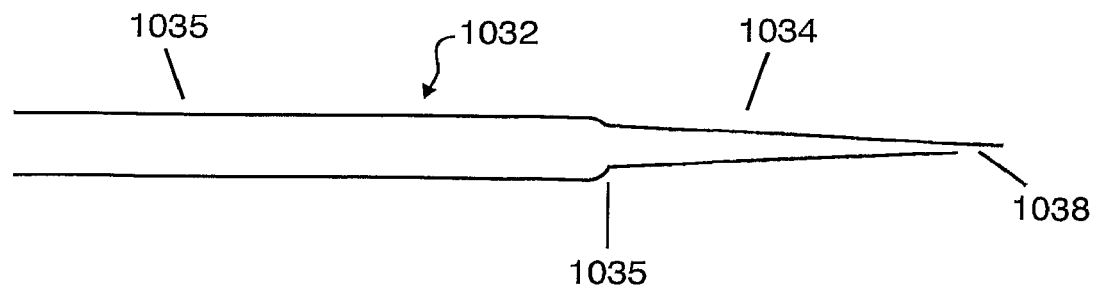
Figure 11:
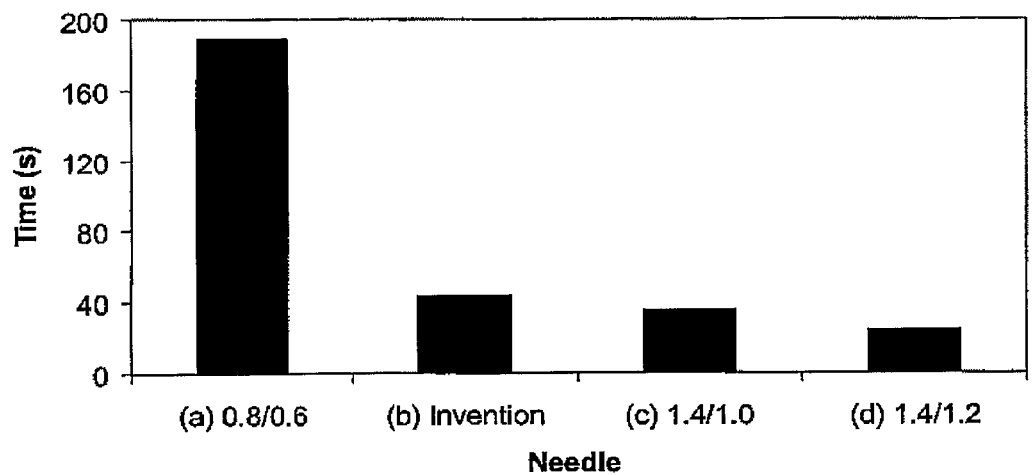
Figure 12:
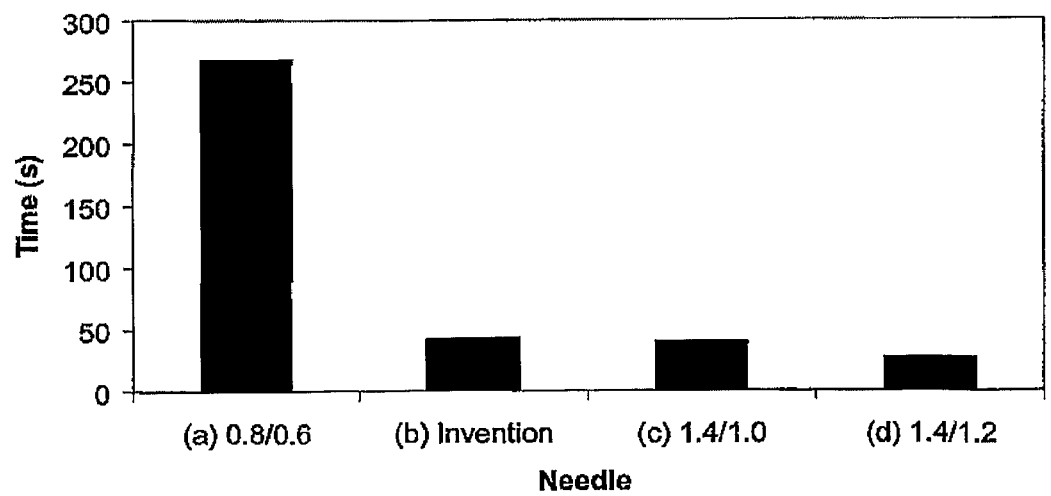
Figure 13:
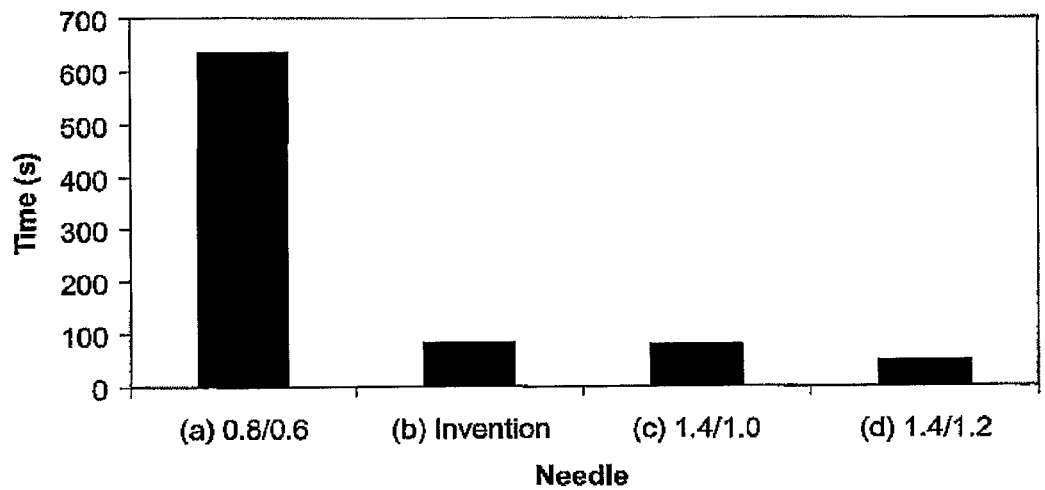
Figure 14:
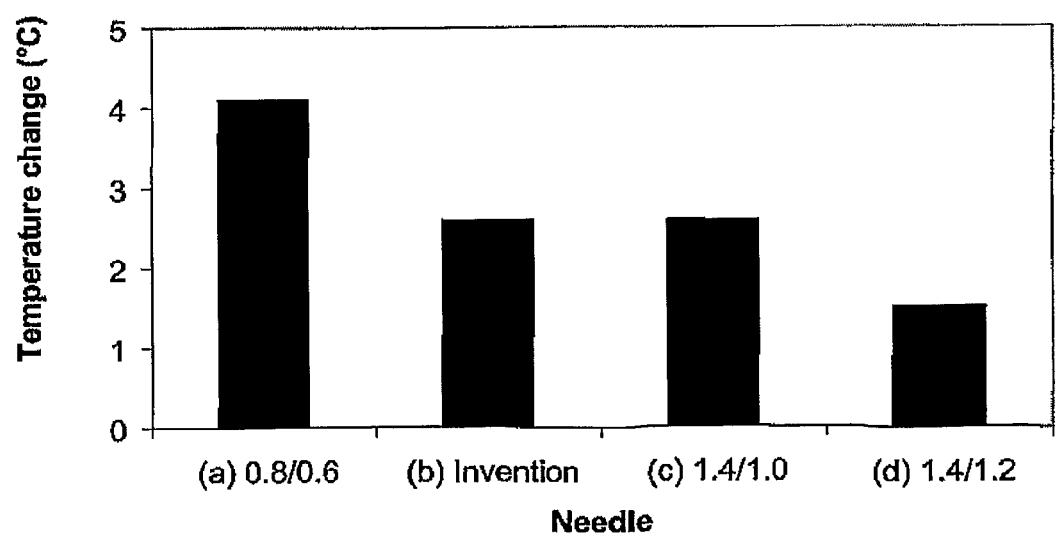
Figure 15:
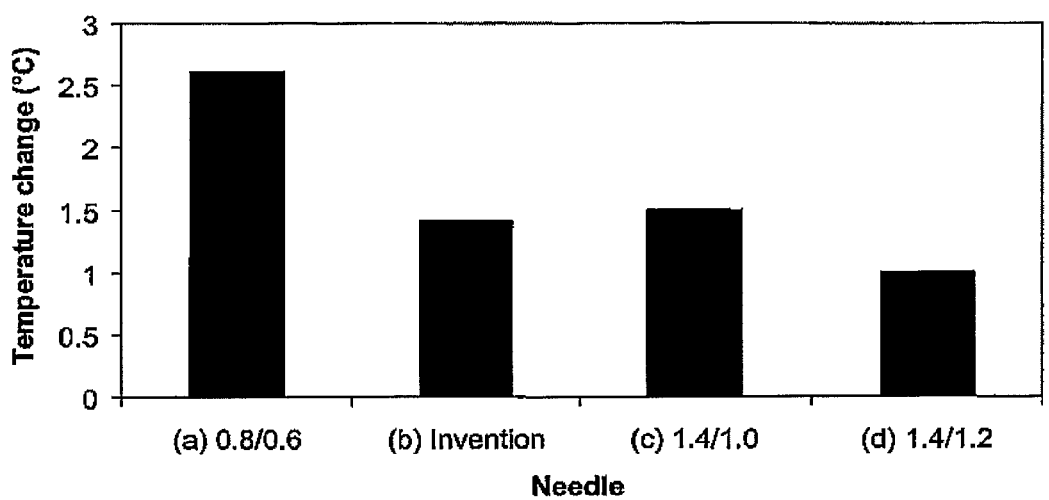

Needles and methods in accordance with the invention will be described, by way of example only, with reference to the further drawings, FIGS. 6 to 15 in which:

FIG. 6 is a longitudinal cross section of a single lumen sampling needle according to the invention;

FIG. 7 is a longitudinal cross section of a single lumen needle according to the invention with a tapered region connecting the first tubular region and second tubular region;

FIG. 8 is a longitudinal cross section of a single lumen needle according to the invention with the first tubular region and second tubular region arranged off center;

FIG. 9 is a longitudinal cross section of a single lumen needle according to the invention with a tapered region connecting the first tubular region and second tubular region and the first tubular region and second tubular region arranged off center;

FIG. 10 is a longitudinal cross section of a single lumen needle according to the invention with a tapered first tubular region;

FIG. 11 is a bar chart showing the difference in aspiration time at room temperature for 20 ml samples of water suitable for in vivo injection through needles (a), (b), (c) and (d), the dimensions of which are given in Table 1;

FIG. 12 is a bar chart showing the difference in aspiration time at room temperature for 10 ml samples of sodium hyaluronate (0.2 g.l$^{-1}$) through needles (a), (b), (c) and (d), the dimensions of which are given in Table 1;

FIG. 13 is a bar chart showing the difference in aspiration time at room temperature for 10 ml samples of sodium hyaluronate (0.4 g.l$^{-1}$) through needles (a), (b), (c) and (d), the dimensions of which are given in Table 1;

FIG. 14 is a bar chart showing the reduction in temperature of samples of water suitable for in vivo injection when aspirated through needles (a), (b), (c) and (d), the dimensions of which are given in Table 1; and FIG. 15 is a bar chart showing the reduction in temperature of samples of water suitable for in vivo injection when aspirated through needles (a), (b), (c) and (d), the dimensions of which are given in Table 1. The temperature parameters for the sampling shown in FIG. 15 are different to those for the sampling shown in FIG. 14.

The raw data for FIGS. 11 to 15 are provided in the Appendix.

DESCRIPTION OF THE PREFERRED EMBODIMENTS

FIG. 6 shows a single lumen sampling needle (632) according to the present invention. The needle comprises a first (leading) tubular region (634) in fluid communication with a second (trailing) tubular region (636), the first tubular region (634) comprises a leading end (638) which is a sharp point for insertion into a subject and the second tubular region (636) comprises a trailing end (640) for fluid communication with a fluid containing chamber (not shown). Application of a vacuum to the trailing end (640) of the needle (632) causes fluid to be drawn in the direction of arrow A. The total length (Z) of the needle is about 350 mm. The second tubular region (636) of the needle (632) has a length (X) of 310 mm, an OD of 1.4 mm and an inner diameter of 1.2 mm. The first tubular region (634) of the needle (632) has a length (Y) of 40 mm, an outer diameter of 0.9 mm and an inner diameter of 0.6 mm.

Different arrangements of the first tubular region and second tubular region are possible. Some examples are given in FIGS. 7 to 10.

In the sampling needle (732) of FIG. 7, a first (leading) tubular region (734) and a second (trailing) tubular region (736) are connected via a tapered region (735).

In the sampling needle (832) of FIG. 8, a first (leading) tubular region (834) and a second (trailing) tubular region (836) are off center relative to each other.

In the sampling needle (932) of FIG. 9, a first (leading) tubular region (934) and a second (trailing) tubular region (936) are off center relative to each other. The first (leading) tubular region (934) and the second (trailing) tubular region (936) are connected via a tapered region (935).

In the sampling needle (1032) of FIG. 10, a first (leading) tubular region (1034) is connected to a second (trailing) tubular region (1036) and the first (leading) tubular region tapers from a leading end (1038), which provides a sharp point for insertion into a subject, to the region (1035) at which the first (leading) tubular region (1034) connects to the second (trailing) tubular region (1036).

The sampling needles of FIGS. 6 to 10 can be connected to conventional sample retrieval apparatus including one or more of an ultrasound transducer, a vacuum pump, aspiration tubing, flushing tubing, a collection tube, a stopper for the collection tube, a vacuum pump, a syringe, a needle guide, a fingertip grip and connectors for connecting the tubing to one or more of the collection tube, vacuum pump and syringe such as those described in relation to FIGS. 1 to 5. The sampling needles of FIGS. 6 to 10 may also comprise a heating arrangement to reduce temperature reduction of the sample during and/or following retrieval.

A method of retrieving a sample from a subject, such as retrieval of an oocyte from a subject, comprises insertion of the sampling needle (632) according to FIG. 6 into a subject. The trailing end of the needle (640) is connected to a vacuum via a collection vessel. The leading end of the needle (638) is inserted into the site of the sample to be retrieved from the subject (e.g. for oocyte retrieval, the site is an ovarian follicle). Only a part or the whole of the first tubular region (634) of the sampling needle (632) penetrates the site of the sample. The second tubular region (636) does not penetrate the site of the sample, e.g. the tissue of the subject. Using conventional vacuum apparatus, a vacuum is applied to the trailing end (640) of the sampling needle (632) and this causes the sample to enter the needle in the direction of arrow A. The sample is drawn into the collection vessel (not shown) through the trailing end (640) of the sampling needle (632).

The sampling needles according to FIGS. 7 to 10 may also be used in a method of retrieving a sample from a subject as described herein.

Analysis of Needles According to the Present Invention

Needles according to the invention were analysed in a laboratory setting and in a clinical setting.

Laboratory Analysis

The aspiration time and temperature change of a sample being retrieved using (a) a thin needle, (b) a needle according to the present invention, (c) a standard needle and (d) an adjusted standard needle were analysed. The dimensions of the needles are provided in Table 1.

TABLE 1

| | | Needle | | | |
|---|---|---|---|---|---|
| | Dimensions | (a) Thin needle | (b) Needle according to the invention | (c) Standard needle | (d) Adjusted standard needle |
| First tubular region (comprising leading end) | Length (mm) | n/a | 40 | n/a | n/a |
| | Outer diameter (mm) | n/a | 0.9 | n/a | n/a |
| | Inner diameter (mm) | n/a | 0.6 | n/a | n/a |
| Second tubular region (comprising trailing end) | Length (mm) | n/a | 300 | n/a | n/a |
| | Outer diameter (mm) | n/a | 1.4 | n/a | n/a |
| | Inner diameter (mm) | n/a | 1.2 | n/a | n/a |
| Full length of needle | Length (mm) | 350 | n/a | 355 | 350 |
| | Outer diameter (mm) | 0.8 | n/a | 1.4 | 1.4 |
| | Inner diameter (mm) | 0.6 | n/a | 1.0 | 1.2 | n/a: not applicable

The effect of the needle dimensions on the aspiration time of samples of different viscosities was studied. The samples used were water suitable for in vivo injection (water for injection (WFI)), sodium hyaluronate solution (0.2 g.l$^{-1}$) and sodium hyaluronate (0.4 g.l$^{-1}$). The sodium hyaluronate solution was prepared by dissolving sodium hyaluronate in WFI.

A vacuum pump (Rocket of London, 240 V, 30 W, 50 Hz) was adjusted to −102 mm Hg (−13.6 kPa) and checked with a calibrated pressure meter before each test. A needle was connected to the vacuum pump with 400 mm tubing (ID 1.35 mm) and to a 50 ml test tube, using a 180 cm long piece of PVC tubing, with an ID of 1.35 mm. The test tube (connected to the needle) was placed in a heating block on a table in order to keep a constant distance between the test tube and the floor for all tests. The heating block was adjusted to a desired temperature or turned off. The needle was held vertically throughout the whole test. A timer was started when the needle was inserted into a container holding the sample at room temperature.

For the test of the effect of needle dimension on the aspiration time of WFI, the timer was stopped when 20 ml of the sample had been transferred into the test tube and the test was repeated 5 times for each needle in a randomized sequence. Three needles of each type were used. The temperature of the sample was held at 20±2° C.

For the test of the effect of needle dimension on the aspiration time of sodium hyaluronate solutions, the timer was stopped when 10 ml of the sample had been transferred into the test tube. The test was repeated 5 times for each needle at randomized sequence. Two needles of each type were used. The temperature of the sample was held at 21±1° C.

As shown in FIG. 11 and Table 2, the aspiration time of samples of WFI aspirated using the needle of the invention (needle (b)) is much shorter than the aspiration time using a thin needle (needle (a)). The standard needle (needle (c)) was slightly better in that the aspiration time for 20 ml WFI was 35 seconds compared to 43 seconds for the needle according to the present invention (needle (b)). The adjusted needle (needle (d)) had the fastest aspiration time (20 ml was aspirated in 24 seconds) as expected, since it has the largest (1.2 mm) inner diameter throughout the whole needle.

TABLE 2

Mean aspiration times of samples of WFI using needles (a), (b), (c) and (d). The dimensions of needles (a), (b), (c) and (d) are given in Table 1. Raw data are given in Appendix 1.

| | Needle | | | |
|---|---|---|---|---|
| | (a) Thin needle | (b) Needle according to the invention | (c) Standard needle | (d) Adjusted standard needle |
| Mean aspiration time of 20 ml WFI | 189 sec | 43 sec | 35 sec | 24 sec |

Sodium hyaluronate solution is more viscous than WFI. A higher concentration of sodium hyaluronate solution is more viscous than a lower concentration of sodium hyaluronate solution. As shown in FIGS. 12 and 13, the aspiration time of both 0.2 g.l$^{-1}$ sodium hyaluronate solution and 0.4 g.l$^{-1}$ sodium hyaluronate solution using the needle of the invention (needle (b)) is much shorter than the aspiration time using a thin needle (needle (a)), (Table 3) and (Table 4). The most marked difference in aspiration time was between the thin needle (needles (a)) and the other needles (needles (b), (c) and (d)). At the higher concentration of sodium hyaluronate (i.e. the more viscous solution), there was no significant difference between the aspiration time for the needle of the invention (needle (b)) and the aspiration time for the standard needle (needle (d)). There was a significant difference (Student's t-test (Appendix 1) between the time taken to aspirate sodium hyaluronate (0.2 g.l$^{-1}$) using needles (a), (c) and (d) when compared with the needle according to the invention (needle (b)). Even so, the difference between the needle of the invention (needle (b)) and the standard needle (needle (c)) has no practical implication when aspirating the 0.2 g/l sodium hyaluronate solution as the difference only involves an increase from 40 seconds to 42 seconds. The normal clinical sample size is, for the case of an oocyte aspiration, about 3 to 8 ml and more commonly about 3 to 5 ml. The aspiration in this experiment was done with 10 ml, meaning that aspiration of half the volume which is the clinical case for an oocyte aspiration would in this experimental setting generate a difference in time of only about 1 second.

TABLE 3

Mean aspiration times of samples of sodium hyaluronate (0.2 g l$^{-1}$) using needles (a), (b), (c) and (d). The dimensions of needles (a), (b), (c) and (d) are given in Table 1.

| | Needle | | | |
|---|---|---|---|---|
| | (a) Thin needle | (b) Needle according to the invention | (c) Standard needle | (d) Adjusted standard needle |
| Mean aspiration time of 10 ml Na-Hyaluronate 0.2 g l$^{-1}$ | 267 sec | 42 sec | 40 sec | 26 sec |

TABLE 4

Mean aspiration times of samples of sodium hyaluronate (0.4 g l$^{-1}$) using needles (a), (b), (c) and (d). The dimensions of needles (a), (b), (c) and (d) are given in Table 1.

| | Needle | | | |
|---|---|---|---|---|
| | (a) Thin needle | (b) Needle according to the invention | (c) Standard needle | (d) Adjusted standard needle |
| Mean aspiration time of 10 ml Na-Hyaluronate 0.4 g l-1 | 635 sec | 82 sec | 81 sec | 50 sec |

In order to test the effect of needle dimension on the temperature of the sample being aspirated, a water bath was heated to a sample retrieval temperature of 37±0.5° C. and a heating block was heated to a sample delivery temperature of either 25±0.5° C. or 37±0.5° C. A 50 ml test tube containing 20 ml water was placed into the heating block in order to standardize the temperature. The temperature was checked with a calibrated thermometer (Vi No 017-69) before each test. The timer was started at the same time as the needle was placed into the water bath with heated water (37±0.5° C.). When 20 ml of heated water had been aspirated into the test tube, the timer was stopped, the needle was removed from the water and 20 seconds after the needle was removed the temperature of the water inside the test tube was determined. The difference in temperature before and after aspiration was determined.

The test was repeated 5 times for each needle in a randomized sequence. After each test, the needles were flushed with water at room temperature. Four 50 ml FALCON™ tubes were used as the test tube for the experiment to make sure that each test was started with a tube at room temperature. Two needles of each type were used. FIG. 14 shows that the reduction in temperature of 20 ml samples of WFI when aspirated from a retrieval temperature of 37° C. and delivered to a test tube incubated at 25° C. did not differ when aspirated with a needle according to the invention (needle (b)) and with a standard needle (needle (c)). For both needles (b) and (c), the temperature of the sample was lowered by 2.6° C. (between the point of retrieval and the point of delivery) for both needles despite the standard needle (needle (c)) aspirating at a faster aspiration time than the needle of the invention (needle (b)). The thin needle (needle (a)) induced the largest temperature loss as expected due to the longer aspiration time. There was a significant difference (Student's t-test between temperature reduction of samples of WFI when aspirated from a retrieval temperature of 37° C. to a retrieval temperature of 25° C. with the needle of the invention (needle (b)) compared to the thin needle (needle (a)) and the adjusted standard needle (needle (d)). There was no significant difference between the temperature reduction of samples aspirated with a needle of the invention (needle (b)) and the standard needle (needle (c)).

FIG. 15 shows that the reduction in temperature of 20 ml samples of WFI when aspirated from a retrieval temperature of 37° C. and delivered to a test tube incubated at 37° C. was less than the reduction in temperature when the retrieval temperature was 37° C. and the test tube was incubated at 25° C. These data show that samples retrieved using the needle of the invention (needle (b)) showed a lower temperature reduction than the samples retrieved using the thin needle (needle (a)). Samples retrieved with the needle of the invention (needle (b)) and the standard needle (needle (a))

appear to show the same reduction in temperature despite that the standard needle (needle (a)) aspirates faster.

The data show that samples retrieved with the needle of the invention have faster aspiration times and show a lower reduction in temperature compared with thin needles (OD: 0.8 mm, ID: 0.6 mm. In combination with the lower level of pain associated with needles of small outer diameter, the needle of the invention is beneficial for clinical use. Since oocytes are retrieved, in practice, in a liquid having a higher viscosity than WFI, retrieval of an oocyte using a needle according to the invention is likely to show as short, or almost as short, an aspiration time as retrieval using a standard needle.

The vagina is at body temperature (37° C.). Therefore, use of a sampling needle via the vagina will incubate the sample being retrieved at 37° C. during passage through the vagina and thus reduce temperature loss.

Clinical Analysis

A sampling needle according to the present invention (needle (b) of Table 1) was compared clinically with a standard needle (needle (c) of Table 1). The needles were used to retrieve oocytes from female subjects.

Two IVF clinics in Sweden participated in this clinical trial. For every patient that participated in the evaluation two different kinds of aspiration needles were used. A gynecologist used the needles alternately on different sides of the uterus. A needle according to the present invention (needle (b)) was compared to a standard needle (needle (c)). Because of different appearance of the needles, blinding to the gynecologist was not possible. The study population consisted of a selected number of patients that underwent treatment at the clinics during the study time period. Patients with previous abdominal operations and patients with known endometriosis were excluded. The aspiration process and anesthetic method were done according to clinical standard procedures and were the same for both groups.

To make sure the needle was not affecting the quality of the oocytes, the following data was also collected: number of collected mature oocytes, number of oocytes with normal fertilization (2PN) and early embryo development.

The needles of the invention where reported to be as usable or at least as usable as the standard needle in parameters reflecting easy handling.

Only one of the clinics analyzed the embryo development of the oocytes retrieved with each needle. The results of the analysis are shown in Table 5 and comprise 10 patients with oocytes retrieved according to the protocol described above. The fertilization rate and embryo development up to day 2 for oocytes aspirated with a needle of the invention (needle (b)) was normal compared to the oocytes aspirated with the control needle (needle (c)).

TABLE 5

|  | Test needle (needle (b)) | Control (needle (c)) |
| --- | --- | --- |
| Fertilization rate | 57% | 54% |
| Cleaved embryos on day 2 | 89% | 95% |
| >3-cells embryos on day 2 | 74% | 55% |

This study suggests that aspiration, i.e. retrieval, of oocytes with the needle according to the invention (needle (b)) has no adverse affect on the success of fertilization or embryo development in comparison to aspiration of oocytes with a standard needle (needle (c)).

Appendix: Raw data for FIGS. 11-15 and Tables 2-5.

TABLE 6

Raw data for FIG. 11; Aspiration time (seconds), water for in vivo injection (WFI).

| | Needle 1 | Needle 2 | Needle 3 |
| --- | --- | --- | --- |
| Needle (c): Standard 1.4/1.0 needle | | | |
| Test 1 | 35 | 35 | 34 |
| Test 2 | 34 | 35 | 35 |
| Test 3 | 35 | 34 | 35 |
| Test 4 | 35 | 34 | 34 |
| Test 5 | 35 | 35 | 35 |
| Mean | 35 | 35 | 35 |
| Total mean | | 35 | |
| Needle (a): Thin 0.8/0.6 needle | | | |
| Test 1 | 190 | 188 | 187 |
| Test 2 | 190 | 187 | 189 |
| Test 3 | 191 | 189 | 187 |
| Test 4 | 192 | 190 | 189 |
| Test 5 | 193 | 189 | 188 |
| Mean | 191 | 189 | 188 |
| Total mean | | 189 | |
| Needle (b): Needle of the invention | | | |
| Test 1 | 43 | 43 | 42 |
| Test 2 | 43 | 43 | 43 |
| Test 3 | 44 | 44 | 42 |
| Test 4 | 43 | 44 | 42 |
| Test 5 | 43 | 43 | 42 |
| Mean | 43 | 43 | 42 |
| Total mean | | 43 | |
| Needle (d): Adjusted 1.4/1.2 needle | | | |
| Test 1 | 24 | 24 | 23 |
| Test 2 | 24 | 23 | 24 |
| Test 3 | 23 | 23 | 24 |
| Test 4 | 23 | 24 | 23 |
| Test 5 | 24 | 23 | 24 |
| Mean | 24 | 23 | 24 |
| Total mean | | 24 | |
| Student's t-test | | | |
| 1.4/1.2 versus Invention | | $P < 0.001$ | |
| 0.8/0.6 versus Invention | | $P < 0.001$ | |
| 1.4/1.0 versus Invention | | $P < 0.001$ | |
| 1.4/1.0 versus 1.4/1.2 | | $P < 0.001$ | |
| 1.4/1.0 versus 0.8/0.6 | | $P < 0.001$ | |

TABLE 7

Raw data for FIG. 12; Aspiration time (seconds), sodium hyaluronate [0.2 g/l].

| | Needle 1 | Needle 2 |
| --- | --- | --- |
| Needle (c): Standard 1.4/1.0 needle | | |
| Test 1 | 40 | 41 |
| Test 2 | 40 | 40 |
| Test 3 | 40 | 39 |
| Test 4 | 40 | 39 |
| Test 5 | 41 | 39 |
| Mean | 40 | 40 |
| Total mean | 40 | |
| Needle (a): Thin 0.8/0.6 needle | | |
| Test 1 | 268 | 267 |
| Test 2 | 267 | 260 |
| Test 3 | 269 | 264 |
| Test 4 | 270 | 265 |

TABLE 7-continued

Raw data for FIG. 12; Aspiration time (seconds), sodium hyaluronate [0.2 g/l].

| | Needle 1 | Needle 2 |
|---|---|---|
| Test 5 | 269 | 269 |
| Mean | 269 | 265 |
| Total mean | 267 | |
| Needle (b): Needle of the invention | | |
| Test 1 | 43 | 42 |
| Test 2 | 43 | 41 |
| Test 3 | 43 | 41 |
| Test 4 | 42 | 41 |
| Test 5 | 42 | 41 |
| Mean | 43 | 41 |
| Total mean | 42 | |
| Needle (d): Adjusted 1.4/1.2 needle | | |
| Test 1 | 27 | 25 |
| Test 2 | 27 | 25 |
| Test 3 | 26 | 25 |
| Test 4 | 26 | 25 |
| Test 5 | 26 | 25 |
| Mean | 26 | 25 |
| Total mean | 26 | |
| Student's t-test | | |
| 1.4/1.2 versus Invention | | $P < 0.001$ |
| 0.8/0.6 versus Invention | | $P < 0.001$ |
| 1.4/1.0 versus Invention | | $P < 0.001$ |
| 1.4/1.0 versus 1.4/1.2 | | $P < 0.001$ |
| 1.4/1.0 versus 0.8/0.6 | | $P < 0.001$ |

TABLE 8

Raw data for FIG. 13; Aspiration time (seconds), sodium hyaluronate [0.4 g/l].

| | Needle 1 | Needle 2 |
|---|---|---|
| Needle (c): Standard 1.4/1.0 needle | | |
| Test 1 | 80 | 82 |
| Test 2 | 79 | 81 |
| Test 3 | 80 | 81 |
| Test 4 | 80 | 82 |
| Test 5 | 81 | 81 |
| Mean | 80 | 81 |
| Total mean | 81 | |
| Needle (a): Thin 0.8/0.6 needle | | |
| Test 1 | 647 | 636 |
| Test 2 | 655 | 622 |
| Test 3 | 660 | 621 |
| Test 4 | 639 | 617 |
| Test 5 | 637 | 618 |
| Mean | 648 | 623 |
| Total mean | 635 | |
| Needle (b): Needle of the invention | | |
| Test 1 | 80 | 82 |
| Test 2 | 79 | 83 |
| Test 3 | 80 | 84 |
| Test 4 | 81 | 83 |
| Test 5 | 80 | 83 |
| Mean | 80 | 83 |
| Total mean | 82 | |
| Needle (d): Adjusted 1.4/1.2 needle | | |
| Test 1 | 50 | 49 |
| Test 2 | 50 | 50 |
| Test 3 | 50 | 49 |
| Test 4 | 50 | 50 |
| Test 5 | 50 | 50 |
| Mean | 50 | 50 |
| Total mean | 50 | |

TABLE 8-continued

Raw data for FIG. 13; Aspiration time (seconds), sodium hyaluronate [0.4 g/l].

| | Needle 1 | Needle 2 |
|---|---|---|
| Student's t-test | | |
| 1.4/1.2 versus Invention | | $P < 0.001$ |
| 0.8/0.6 versus Invention | | $P < 0.001$ |
| 1.4/1.0 versus Invention | | $P = 0.213$ |
| 1.4/1.0 versus 1.4/1.2 | | $P < 0.001$ |
| 1.4/1.0 versus 0.8/0.6 | | $P < 0.001$ |

TABLE 9

Raw data for FIG. 14; Aspiration temperature change test, 20 ml WFI at 37° C. to 25° C.

| | Needle 1 | Needle 2 |
|---|---|---|
| Needle (c): Standard 1.4/1.0 needle | | |
| Test 1 | 2.6 | 2.6 |
| Test 2 | 2.4 | 2.8 |
| Test 3 | 2.6 | 2.7 |
| Test 4 | 2.5 | 2.7 |
| Test 5 | 2.5 | 2.6 |
| Mean | 2.5 | 2.7 |
| Total mean | 2.6 | |
| Needle (a): Thin 0.8/0.6 needle | | |
| Test 1 | 4.3 | 3.9 |
| Test 2 | 4.1 | 4.1 |
| Test 3 | 4.2 | 4.0 |
| Test 4 | 4.0 | 3.9 |
| Test 5 | 4.1 | 4.0 |
| Mean | 4.1 | 4.0 |
| Total mean | 4.1 | |
| Needle (b): Needle of the invention | | |
| Test 1 | 2.7 | 2.6 |
| Test 2 | 2.8 | 2.5 |
| Test 3 | 2.7 | 2.5 |
| Test 4 | 2.7 | 2.6 |
| Test 5 | 2.7 | 2.6 |
| Mean | 2.7 | 2.6 |
| Total mean | 2.6 | |
| Needle (d): Adjusted 1.4/1.2 needle | | |
| Test 1 | 1.4 | 1.5 |
| Test 2 | 1.8 | 1.5 |
| Test 3 | 1.5 | 1.4 |
| Test 4 | 1.9 | 1.3 |
| Test 5 | 1.4 | 1.3 |
| Mean | 1.6 | 1.4 |
| Total mean | 1.5 | |
| Student's t-test | | |
| 1.4/1.2 versus Invention | | $P < 0.001$ |
| 0.8/0.6 versus Invention | | $P < 0.001$ |
| 1.4/1.0 versus Invention | | $P = 0.412$ |
| 1.4/1.0 versus 1.4/1.2 | | $P < 0.001$ |
| 1.4/1.0 versus 0.8/0.6 | | $P < 0.001$ |

TABLE 10

Raw data for FIG. 15; Aspiration temperature change test, 20 ml WFI at 37° C. to 37° C.

| | Needle 1 | Needle 2 |
|---|---|---|
| Needle (c): Standard 1.4/1.0 needle | | |
| Test 1 | 1.5 | 1.6 |
| Test 2 | 1.6 | 1.5 |

TABLE 10-continued

Raw data for FIG. 15; Aspiration temperature change test, 20 ml WFI at 37° C. to 37° C.

|  | Needle 1 | Needle 2 |
|---|---|---|
| Test 3 | 1.5 | 1.5 |
| Test 4 | 1.4 | 1.3 |
| Test 5 | 1.3 | 1.3 |
| Mean | 1.5 | 1.4 |
| Total mean | 1.5 | |
| Needle (a): Thin 0.8/0.6 needle | | |
| Test 1 | 2.5 | 2.9 |
| Test 2 | 2.6 | 2.6 |
| Test 3 | 2.3 | 2.6 |
| Test 4 | 2.7 | 2.6 |
| Test 5 | 2.5 | 2.6 |
| Mean | 2.5 | 2.7 |
| Total mean | 2.6 | |
| Needle (b): Needle of the invention | | |
| Test 1 | 1.4 | 1.7 |
| Test 2 | 1.3 | 1.4 |
| Test 3 | 1.3 | 1.4 |
| Test 4 | 1.3 | 1.4 |
| Test 5 | 1.3 | 1.4 |
| Mean | 1.3 | 1.5 |
| Total mean | 1.4 | |
| Needle (d): Adjusted 1.4/1.2 needle | | |
| Test 1 | 1.2 | 0.9 |
| Test 2 | 1.2 | 0.8 |
| Test 3 | 1.2 | 0.8 |
| Test 4 | 1.2 | 0.9 |
| Test 5 | 1.2 | 0.8 |
| Mean | 1.2 | 0.8 |
| Total mean | 1.0 | |
| Student's t-test | | |
| 1.4/1.2 versus Invention | | $P < 0.001$ |
| 0.8/0.6 versus Invention | | $P < 0.001$ |
| 1.4/1.0 versus Invention | | $P = 0.274$ |
| 1.4/1.0 versus 1.4/1.2 | | $P < 0.001$ |
| 1.4/1.0 versus 0.8/0.6 | | $P < 0.001$ |

TABLE 11

Comparison of the effect of needle dimensions on fertilization and embryo development of oocytes harvested using a control needle (needle (c): outer diameter 1.4 mm, inner diameter 1.0 mm) and a test needle according to the invention (needle (b)).

| Treatment No. | Needle (test or control = single lumen) | Method of fertilization (ICSI or IVF) | # collected oocytes | Fertilization #mature oocytes (MII) (in case of ICSI) | # fertilized oocytes (Sum of 1, 2 and 3 PN) | #2 PN | Development Day 2 # cleaved embryos | # 2-cell embryos | # 3-cell embryos | # 4-cell embryos | # >4-cell embryos |
|---|---|---|---|---|---|---|---|---|---|---|---|
| 1b | c | IVF | 2 | | 2 | 1 | 1 | 1 | | | |
| 2a | c | IVF | 4 | | 3 | 2 | 2 | 1 | 1 | | |
| 3b | c | IVF | 3 | | 3 | 3 | 3 | 1 | | 2 | |
| 4a | c | IVF | 1 | | 1 | 1 | 1 | | | 1 | |
| 5a | c | IVF | 7 | | 4 | 4 | 4 | 4 | | | |
| 6b | c | IVF | 3 | | 2 | 2 | 1 | | | 1 | |
| 7a | c | ICSI (TESA) | 3 | 2 | 1 | 1 | 1 | 1 | | | |
| 8a | c | ICSI | 6 | 3 | 2 | 2 | 2 | | | 2 | |
| 9b | c | IVF | 11 | | 5 | 5 | 5 | | | 4 | 1 |
| 10a | c | ICSI (TESA) | 6 | 5 | 1 | 1 | 1 | | | 1 | |
| | | | 46 | 41 | 22 | 21 | 8 | 1 | 11 | 1 | |
| 1a | t | IVF | 1 | | 1 | 1 | 1 | 1 | | | |
| 2b | t | IVF | 6 | | 5 | 5 | 5 | 1 | | 3 | 1 |
| 3a | t | IVF | 3 | | 2 | 2 | 2 | | | 2 | |
| 4b | t | IVF | 3 | | 3 | 3 | 3 | | | 2 | 1 |
| 5b | t | IVF | 4 | | 3 | 3 | 3 | 2 | | 1 | |
| 6a | t | IVF | 5 | | 2 | 2 | 1 | | | 1 | |
| 7b | t | ICSI (TESA) | 3 | 3 | 0 | 0 | 0 | | | | |
| 8b | t | ICSI | 8 | 6 | 4 | 4 | 4 | | | 3 | 1 |
| 9a | t | IVF | 10 | | 6 | 6 | 4 | | | 4 | |
| 10b | t | ICSI (TESA) | 7 | 6 | 1 | 1 | 1 | | | 1 | |
| | | | 50 | 47 | 27 | 24 | 4 | 0 | 17 | | |

The invention claimed is:

1. An oocyte retrieval needle comprising a first tubular region in fluid communication with a second tubular region, the first tubular region comprising a sharp point leading end configured for insertion into a subject and the second tubular region comprising an open trailing end, the leading end and the trailing end forming respective opposite ends of the needle, wherein:
    internal passages of the first and second tubular regions form a continuous open passage extending from the leading end to the trailing end;
    the first tubular region has an outer diameter which is less than an outer diameter of the second tubular region and the internal passage of the first tubular region has an inner, luminal diameter which is less than an inner diameter of the internal passage of the second tubular region;
    the first tubular region and the second tubular region have a combined length of from 150 mm to 500 mm, and the first tubular region has a length of from 30 mm to 100 mm;
    the first tubular region and the second tubular region are formed from one or more materials selected from stainless steel, carbon fibre, hard plastics, ceramic, or glass; and
    the oocyte retrieval needle is a double lumen needle.

2. The oocyte retrieval needle according to claim 1, wherein the oocyte retrieval needle has a central axis, and the first tubular region and the second tubular region are arranged along the central axis.

3. The oocyte retrieval needle according to claim 1, wherein the sharp point leading end is echogenic.

4. The oocyte retrieval needle according to claim 1, wherein the inner, luminal diameter of the internal passage of the first tubular region is greater than or equal to 0.2 mm and less than the inner diameter of the internal passage of the second tubular region.

5. The oocyte retrieval needle according to claim 1, wherein the inner, luminal diameter of the internal passage of the first tubular region is greater than or equal to 0.4 mm and less than the inner diameter of the internal passage of the second tubular region.

6. The oocyte retrieval needle according to claim 1, wherein the inner, luminal diameter of the internal passage of the first tubular region is greater than or equal to 0.6 mm and less than the inner diameter of the internal passage of the second tubular region.

7. The oocyte retrieval needle according to claim 1, wherein the inner diameter of the internal passage of the second tubular region is 0.9 mm.

8. The oocyte retrieval needle according to claim 1, wherein the inner diameter of the internal passage of the second tubular region is 1.1 mm.

9. The oocyte retrieval needle according to claim 1, wherein the inner diameter of the internal passage of the second tubular region is 1.2 mm.

10. The oocyte retrieval needle according to claim 1, wherein the outer diameter of the first tubular region is from 0.6 mm to 1.2 mm.

11. The oocyte retrieval needle according to claim 10, wherein the outer diameter of the first tubular region is from 0.8 mm to 1.0 mm.

12. The oocyte retrieval needle according to claim 11, wherein the outer diameter of the first tubular region is 0.9 mm.

13. The oocyte retrieval needle according to claim 1, wherein the outer diameter of the second tubular region is 1.1 mm.

14. The oocyte retrieval needle according to claim 1, wherein the outer diameter of the second tubular region is 1.2 mm.

15. The oocyte retrieval needle according to claim 1, wherein the outer diameter of the second tubular region is 1.4 mm.

16. The oocyte retrieval needle according to claim 1, wherein the first tubular region and the second tubular region are connected via a tapered region.

17. The oocyte retrieval needle according to claim 1, wherein the first and second tubular regions have a combined length of from 200 mm to 400 mm.

18. The oocyte retrieval needle according to claim 1, wherein the length of the first tubular region is 40 mm to 60 mm.

19. The oocyte retrieval needle according to claim 1, wherein the first tubular region is formed from one or more stainless steels selected from AISI 304, AISI 316, SIS 2346 and SIS 2543.

20. The oocyte retrieval needle according to claim 1, wherein the second tubular region comprises stainless steel selected from AISI 304, AISI 316, SIS 2346 and SIS 2543.

21. The oocyte retrieval needle according to claim 1, wherein the first tubular region and the second tubular region are formed from a single piece of material.

22. A method of retrieving an oocyte from a subject comprising:
    inserting an oocyte retrieval needle into a site on the subject from which the oocyte is to be retrieved; and
    withdrawing the oocyte from the subject by aspiration through the oocyte retrieval needle, wherein
    the oocyte retrieval needle comprises a first tubular region in fluid communication with a second tubular region, the first tubular region comprising a sharp point leading end configured for insertion into the subject and the second tubular region comprising an open trailing end, the leading end and the trailing end forming respective opposite ends of the needle, wherein:
    internal passages of the first and second tubular regions form a continuous open passage extending from the leading end to the trailing end;
    the first tubular region has an outer diameter which is less than an outer diameter of the second tubular region and the internal passage of the first tubular region has an inner, luminal diameter which is less than an inner diameter of the internal passage of the second tubular region;
    the first tubular region and the second tubular region have a combined length of from 150 mm to 500 mm, and the first tubular region has a length of from 30 mm to 100 mm;
    the first tubular region and the second tubular region are formed from one or more materials selected from stainless steel, carbon fibre, hard plastics, ceramic, or glass; and
    the oocyte retrieval needle is a double lumen needle.

23. The method according to claim 22, wherein the first tubular region of the oocyte retrieval needle penetrates a vaginal wall, an ovary, and a follicle of the subject, and the second tubular region of the oocyte retrieval needle does not penetrate the vaginal wall, the ovary, or the follicle of the subject.

24. The method according to claim 22, wherein the subject is a human.

25. The method according to claim 22, further comprising flushing a flushing medium into the oocyte retrieval needle.

26. The method according to claim 25, wherein the flushing medium is flushed into the oocyte retrieval needle through flushing tubing.

27. The method according to claim 22, further comprising collecting the oocyte in a fluid container.

28. The method according to claim 27, wherein the fluid container is separate from the oocyte retrieval needle and is coupled to the open trailing end so as to place an interior of the fluid container in fluid communication with the continuous open passage.

29. The method according to claim 28, wherein the fluid container comprises a test tube, and the open trailing end and the test tube are coupled by aspiration tubing.

* * * * *